United States Patent
Wang

(10) Patent No.: US 9,669,070 B2
(45) Date of Patent: Jun. 6, 2017

(54) TREATMENT AND PREVENTION OF RADIATION INJURY USING MFG-E8

(71) Applicant: The Feinstein Institute For Medical Research, Manhasset, NY (US)

(72) Inventor: Ping Wang, Roslyn, NY (US)

(73) Assignee: The Feinstein Institute For Medical Research, Manhasset, NY (US)

( * ) Notice: Subject to any disclaimer, the term of this patent is extended or adjusted under 35 U.S.C. 154(b) by 0 days.

(21) Appl. No.: 14/481,959

(22) Filed: Sep. 10, 2014

(65) Prior Publication Data
US 2015/0080304 A1 Mar. 19, 2015

Related U.S. Application Data

(60) Provisional application No. 61/878,705, filed on Sep. 17, 2013.

(51) Int. Cl.
*A61K 38/18* (2006.01)
(52) U.S. Cl.
CPC .................. *A61K 38/1808* (2013.01)
(58) Field of Classification Search
None
See application file for complete search history.

(56) References Cited

U.S. PATENT DOCUMENTS

| | | | | |
|---|---|---|---|---|
| 5,972,337 A | * | 10/1999 | Ceriani | A61K 47/48584 424/185.1 |
| 2008/0027007 A1 | * | 1/2008 | Benner | A61K 38/08 514/21.5 |
| 2009/0297498 A1 | | 12/2009 | Wang | |
| 2011/0105399 A1 | | 5/2011 | Wang | |
| 2014/0121163 A1 | | 5/2014 | Wang | |

OTHER PUBLICATIONS

Wolbarst et al., Radiology, 254(3):660-677, 2010.*
Francois et al.,Hindawi Publishing Corporation, BioMed Research International, vol. 2013, Article ID 123241, 9 pages, http://dx.doi.org/10.1155/2013/123241.*
Ajakaiye Ma et al. "Recombinant Human MFG-E8 Attenuates Intestinal Injury and Mortality in Severe Whole Body Irradiation in Rats", PLoS One 7(10): e46540 (9 pages), Oct. 8, 2012.
Aziz M et al. "Milk Fat Globule-Epidermal Growth Factor—Factor 8 Attenuates Neutrophil Infiltration in Acute Lung Injury via Modulation of CXCR2", J. Immunol 2012; 189:393-402, Epub May 25, 2012.
Aziz M et al. "Pre-Treatment of Recombinant Mouse MFG-E8 Downregulates LPS-Induced TNF-α Production in Macrophages via STATS-Mediated SOCS3 Activation", PLoS one 6(11): e27685 (12 pages, Nov. 15, 2011.
Aziz M et al. "Review: milk fat globule-EGF factor 8 expression, function and plausible signal transduction in resolving inflammation" Apoptosis Nov. 2011; 16(11):1077-86 (Abstract only).
Cui T et al. "Milk fat globule epidermal growth factor 8 attenuates acute lung injury in mice after intestinal ischemia and reperfusion", Am. J. Respir. Crit. Care Med. Feb. 1, 2010; 181(3):238-46. Epub Nov. 5, 2009.
Komura H et al. "Milk Fat Globule Epidermal Growth Factor-Factor VIII is Down-Regulated in Sepsis via the Lipopolysaccharide-CD14 Pathway", J. Immunol 2009; 182:581-587.
Matsuda A et al. "Milk Fat Globule-EGF Factor VIII Ameliorates Liver Injury after Hepatic Ischemia-Reperfusion", J. Surg. Res. Mar. 2013; 180(1): e37-e46.
Matsuda A et al. "Protective effect of milk fat globule-EGF factor VIII after renal ischemia-reperfusion injury in mice", Crit. Care Med. Sep. 2011; 39(9):2039-2047.
Matsuda A et al. "Milk fat globule-EGF factor VIII in sepsis and ischemia-reperfusion injury", Mol. Med. Jan.-Feb. 2011; 17(1-2):126-33. Epub Sep. 21, 2010.
Matsuda A et al. "Novel Therapeutic Targets for Sepsis: Regulation of Exaggerated Inflammatory Responses", J Nippon Med Sch. 2012; 79(1): 4-18.
Miksa M et al. "Immature Dendritic Cell-Derived Exosomes Rescue Septic Animals Via Milk Fat Globule Epidermal Growth Factor VIII", J. Immunol 2009; 183:5983-5990.
Miksa M et al. "Fractalkine-induced MFG-E8 leads to enhanced apoptotic cell clearance by macrophages", Mol. Med. Nov.-Dec. 2007; 13(11-12):553-60.
Miksa M et al. "Dendritic cell-derived exosomes containing milk fat globule epidermal growth factor-factor VIII attenuate proinflammatory responses in sepsis", Shock Jun. 2006; 25(6):586-93 (Abstract only).
Shah KG et al. "Recombinant human milk fat globule-EGF factor 8 produces dose-dependent benefits in sepsis", Intensive Care Med. Jan. 2012; 38(1):128-36. Epub Sep 23, 2011. (Abstract only).
Wu Ret al. "Enhancing apoptotic cell clearance mitigates bacterial translocation and promotes tissue repair after gut ischemia-reperfusion injury", International Journal of Molecular Medicine 2012; 30:593-598.
Wu R et al. "Milk fat globule EGF factor 8 attenuates sepsis-induced apoptosis and organ injury in alcohol-intoxicated rats", Alcohol Clin. Exp. Res. Sep. 1, 2010; 34(9):1625-33. Epub Jun. 25, 2010.
Qiang X et al. "Expression and Characterization of Recombinant Human Milk Fat Globule-EGF factor VIII", Int. J. Mol. Med. Dec. 2011; 28(6):1071-6. Epub Aug. 26, 2011. (Abstract only).
Zhang F et al. "Milk Fat Globule EGF-Factor 8 Mitigates Inflammation and Tissue Injury After Hemorrhagic Shock in Experimental Animals" J. Trauma Acute Care Surg. Apr. 2012; 72(4):861-869.

* cited by examiner

*Primary Examiner* — Marianne P Allen
(74) *Attorney, Agent, or Firm* — Amster, Rothstein & Ebenstein LLP

(57) ABSTRACT

Methods and compositions are disclosed for treating and preventing radiation injury using milk fat globule epidermal growth factor-factor VIII (MFG-E8).

10 Claims, 10 Drawing Sheets

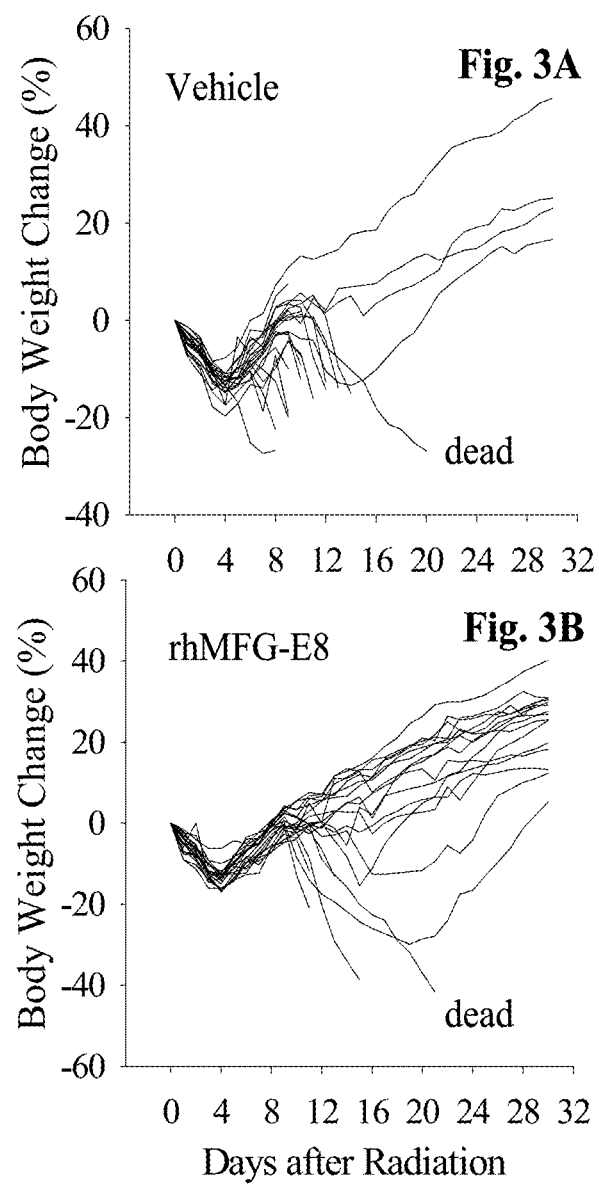

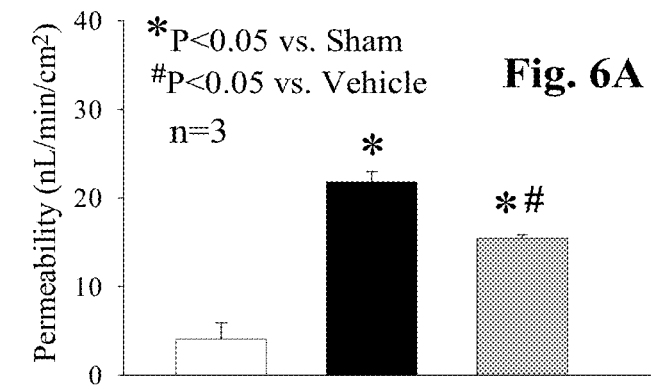
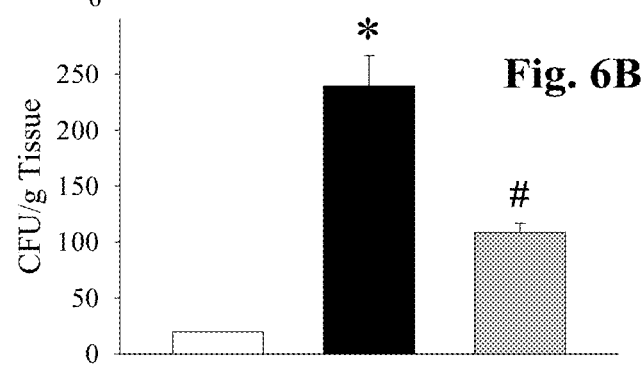
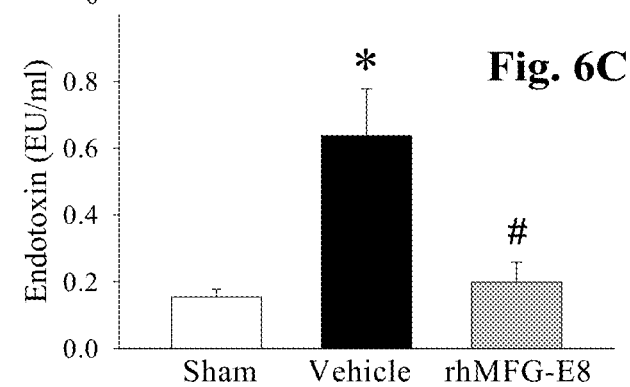

TREATMENT AND PREVENTION OF RADIATION INJURY USING MFG-E8

CROSS-REFERENCE TO RELATED APPLICATION

This application claims the benefit of U.S. Provisional Patent Application No. 61/878,705, filed Sep. 17, 2013, the contents of which are herein incorporated by reference in their entirety.

STATEMENT OF GOVERNMENT SUPPORT

This invention was made with government support under grant numbers GM057468 and AI080536 awarded by the National Institutes of Health. The government has certain rights in the invention.

BACKGROUND OF THE INVENTION

Throughout this application various publications are referred to in brackets. Full citations for these references may be found at the end of the specification. The disclosures of these publications are hereby incorporated by reference in their entirety into the subject application to more fully describe the art to which the subject invention pertains.

The current widespread use of radioactive materials has resulted in the realization of serious and dangerous effects of radiation exposure. As evidenced by the Chernobyl nuclear disaster of 1986 and more recently with the massive radiation leak at the Fukushima I power plant, massive unforeseen radiation exposure is a possibility that must be planned for and mitigated. This is further necessitated by the risk of nuclear warfare or the utilization of a "dirty bomb" by terrorists. Major strides have been made in minimizing the effects of planned radiation exposure, especially in radiology and radiotherapy. Radio-protectors have been developed which have shown efficacy in animal and human studies, and one of these radio-protectors, amifostine, is already in clinical use [1-3]. However, amifostine is limited by its route of administration and toxicity, which would minimize its usefulness in the event of an imminent nuclear disaster. Therefore, there is an unmet need in the development of effective mitigators of radioactive damage.

Acute radiation syndrome (ARS) is an acute illness caused by rapid exposure of most or all of the body to a high dose of penetrating radiation. Its major cause is the depletion of immature parenchymal stem cells in specific tissues. The gastrointestinal (GI) syndrome, one of the three classic ARS syndromes, contributes significantly to early mortality and several debilitating complications that follow severe acute radiation exposure. Occurrence of the GI syndrome is associated with extremely low survival: destructive and irreparable changes occur in the GI tract with loss of intestinal crypts and breakdown of the mucosal barrier. At higher radiation doses, the mortality rate of the gastrointestinal syndrome exceeds that of the hematopoietic syndrome with most victims dying within 2 weeks [4,5].

Milk fat globule-EGF factor 8 (MFG-E8) is a secreted integrin-binding glycoprotein that was first identified as one of the major proteins associated with the milk fat globule membrane in the mouse mammary epithelium [6]. MFG-E8 is widely expressed in different species [7,8]. The human homolog contains 387 amino acids and has been identified by several other names including Lactadherin, SED1 and BA46. Mouse MFG-E8 consists of two-repeated EGF-like domains, a mucin-like domain, and two-repeated discoidin-like domains (C-domains); it contains an integrin-binding motif (RGD sequence) and is reported to have two splice variants. A longer splice variant is expressed in a lactation-dependent manner in mammary tissues while the shorter splice variant is expressed ubiquitously in many tissues. MFG-E8 is a potent opsonin for the clearance of apoptotic cells. It is produced by mononuclear cells of immune-competent organs including the spleen and the liver. MFG-E8 is known to participate in a wide variety of cellular interactions, including phagocytosis of apoptotic cells, adhesion between sperm and the egg coat, repair of intestinal mucosa, mammary gland branching morphogenesis and angiogenesis [8-11].

Increasing danger of nuclear attacks, accidents and potential terrorism has caused major concern towards radiation exposure, and development of therapies for radiation mitigation is of significant value. Gastrointestinal injuries due to radiation exposure cause high mortality, and intestinal crypt cells are extremely sensitive to radiation. Cell proliferation, differentiation, and migration are crucial events required for the maintenance of an intact epithelial layer. MFG-E8 plays an important role in the maintenance of intestinal epithelial homeostasis and the promotion of mucosal healing [7,12-14], which are essential attributes in mitigation of GI impairment after ionizing radiation.

The present invention addresses the need for treatment and prevention of adverse effects of radiation exposure using MFG-E8.

SUMMARY OF THE INVENTION

The present invention provides methods of treating radiation damage in a subject exposed to radiation above ambient levels or preventing radiation damage in a subject at risk for exposure to radiation above ambient levels comprising administering to the subject a milk fat globule epidermal growth factor-factor VIII (MFG-E8) in an amount effective to treat or prevent radiation damage in a subject.

The invention provides methods of preparing a pharmaceutical composition for preventing and/or treating radiation damage in a subject, where the methods comprise formulating milk fat globule epidermal growth factor-factor VIII (MFG-E8) in a pharmaceutical composition in an amount effective to prevent and/or treat radiation damage in a subject.

The invention also provides pharmaceutical compositions comprising milk fat globule epidermal growth factor-factor VIII (MFG-E8) in dosage form for preventing and/or treating radiation damage in a subject, and a pharmaceutically acceptable carrier.

The invention further provides pharmaceutical products comprising a milk fat globule epidermal growth factor-factor VIII (MFG-E8) formulated in a pharmaceutically acceptable carrier; and a package insert providing instructions for the administration of MFG-E8 for the prevention and/or treatment of radiation damage in a subject.

BRIEF DESCRIPTION OF THE DRAWINGS

FIG. 3A-3B. Post-exposure administration of rhMFG-E8 prevents body weight (BW) loss after WBI. Body weight change (%) after WBI (10-Gy) in vehicle group (A) and rhMFG-E8-treated group (B). Each rat depicted by a single line.

FIG. 6A-6C. rhMFG-E8 (daily for 7 days, starting at 24 hours after exposure to WBI) attenuates the increased gut permeability and endotoxemia induced by WBI. Effects on gut permeability (A), bacterial count (B) and serum endotoxin levels (C). Ileal segments were harvested from WBI rats at day 9 post-exposure.

DETAILED DESCRIPTION OF THE INVENTION

Figures 1A, 1B:
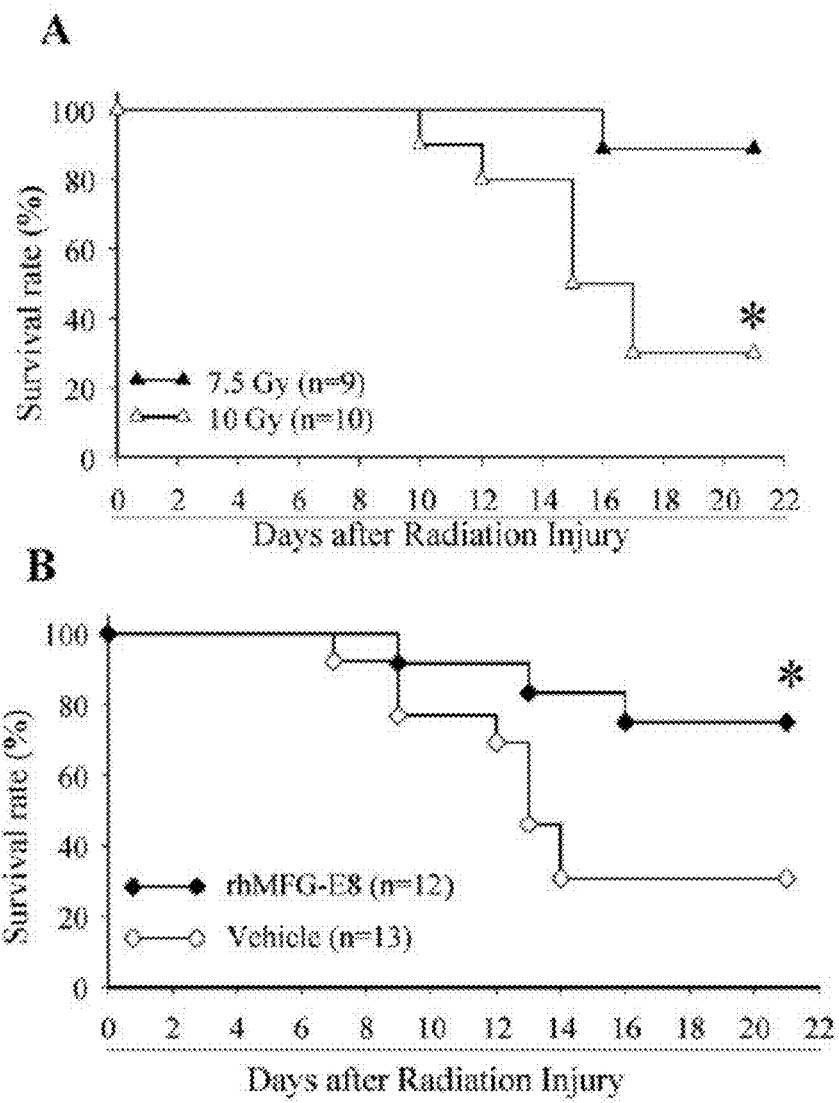
FIG. 1A-1B. $LD_{70}/21$ and rhMFG-E8 survival curves. (A) Male Sprague-Dawley rats were subjected to whole body irradiation (WBI) using 7.5 and 10 Gy, and observed for 21 days. (B) Rats underwent WBI using 10 Gy, treated with rhMFG-E8 (daily for 3 days, starting at 6 hours after exposure to WBI) or Vehicle and observed for 21 days. The survival rate was estimated by the Kaplan-Meier method and compared by Log Rank test. * P<0.05 vs. 7.5 Gy (FIG. 1A) or Vehicle (FIG. 1B).

The present invention provides a method of treating radiation damage in a subject exposed to radiation above ambient levels or preventing radiation damage in a subject at risk for exposure to radiation above ambient levels comprising administering to the subject a milk fat globule epidermal growth factor-factor VIII (MFG-E8) in an amount effective to treat or prevent radiation damage in a subject.

A subject who is at risk for exposure to radiation can be, for example, a subject who is about to enter a region that contains, or is thought to contain, radiation above ambient levels, such as, for example, the vicinity of a nuclear reactor or terrorist attack. The subject at risk for exposure to radiation can be, for example, about to undergo radiation therapy for treatment of a disease, such as cancer.

The radiation that the subject is exposed to or is at risk for exposure to can be, for example, radiation from warfare or a terrorist attack, a radiation leak from an atomic reactor, space travel or radiation therapy.

The radiation can be, for example, whole body irradiation or radiation of only a portion of the body. The radiation can be, for example, ionizing irradiation. The radiation can be, for example, one or more of gamma radiation, x-ray radiation, solar radiation in space, cosmic radiation, electromagnetic radiation, bremsstrahlung radiation, ultraviolet radiation, and particulate radiation (e.g., α-radiation and β-radiation). The source of the radiation can be, for example, a medical isotope, nuclear reactor, or weapon.

As used herein, to "treat" radiation damage in a subject means to reduce or prevent an effect of radiation. For example, treatment of the subject with MFG-E8 can reduce or prevent a decrease in body weight following exposure to radiation, and/or reduce or prevent a decrease in MFG-E8 gene expression following exposure to radiation, and/or reduce or prevent damage or changes to intestinal structure and/or function, such as gut permeability, following exposure to radiation. Preferably, treatment of the subject with MFG-E8 increases the subject's chance of survival following exposure to radiation.

MFG-E8 can be administered to a subject at risk for exposure to radiation before the subject is exposed to the radiation. For a subject who has been exposed to radiation, MFG-E8 can be administered as soon as possible following exposure to radiation. Preferably, MFG-E8 is administered to a subject within 48 hours after exposure to radiation. More preferably, MFG-E8 is administered to a subject within 24 hours after exposure to radiation.

The invention provides a method of preparing a pharmaceutical composition for preventing and/or treating radiation damage in a subject, the method comprising formulating milk fat globule epidermal growth factor-factor VIII (MFG-E8) in a pharmaceutical composition in an amount effective to prevent and/or treat radiation damage in a subject.

The invention also provides a pharmaceutical composition comprising milk fat globule epidermal growth factor-factor VIII (MFG-E8) in dosage form for preventing and/or treating radiation damage in a subject, and a pharmaceutically acceptable carrier.

The invention further provides a pharmaceutical product comprising a milk fat globule epidermal growth factor-factor VIII (MFG-E8) formulated in a pharmaceutically acceptable carrier; and a package insert providing instructions for the administration of MFG-E8 for the prevention and/or treatment of radiation damage in a subject.

In a preferred embodiment of any of the methods, compositions, products or uses described herein, the MFG-E8 is human MFG-E8. Preferably, the human MFG-E8 is a recombinant human MFG-E8 (rhMFG-E8). Different recombinant protein production platforms can be used to produce rhMFG-E8, including for example, bacteria, yeasts, plants, insect cells, or mammalian cells. In different embodiments, the rhMFG-E8 has an amino acid sequence that is at least 95% identical to human MFG-E8 (hMFG-E8) (SEQ ID NO:1), or that is at least 99% identical to human MFG-E8 (hMFG-E8) (SEQ ID NO:1), or that is identical to human MFG-E8 (hMFG-E8) (SEQ ID NO:1). For example, one or more amino acids in SEQ ID NO:1 can be mutated or substituted with a different amino acid.

In different embodiments, the MFG-E8 can have an amino acid sequence that is at least 95% identical to human MFG-E8 (SEQ ID NO:2), or that is at least 99% identical to human MFG-E8 (SEQ ID NO:2), or that is identical to SEQ ID NO:2. For example, one or more amino acids in SEQ ID NO:2 can be mutated or substituted with a different amino acid.

In a preferred embodiment, the MFG-E8 is non-glycosylated. Different recombinant protein production platforms can be used to produce non-glycosylated rhMFG-E8, including for example, bacteria, yeasts, plants, insect cells, or mammalian cells.

Amino acid sequences for human and mouse MFG-E8 are shown below. SEQ ID NO:2—human MFG-E8—from GenBank NP005919:

```
  1    mprprllaal  cgallcapsl  lvaldicskn
       pchngglcee  isqevrgdvf  psytctclkg
 61    yagnhcetkc  veplgmengn  iansqiaass
       vrvtflglqh  wvpelarinr  agmvnawtps
121    snddnpwiqv  nllrrmwvtg  vvtqgasrla
       sheylkafkv  ayslnghefd  fihdvnkkhk
181    efvgnwnkna  vhvnlfetpv  eaqyvrlypt
       schtactlrf  ellgcelngc  anplglknns
241    ipdkqitass  syktwglhlf  swnpsyarld
       kqgnfnawva  gsygndqwlq  vdlgsskevt
301    giitqgarnf  gsvqfvasyk  vaysndsanw
       teyqdprtgs  skifpgnwdn  hshkknlfet
361    pilaryvril  pvawhnrial  rlellgc.
```

Human MGF-E8 protein is synthesized as the 387 amino acid precursor shown above that contains a 23 amino acid signal sequence and a 364 amino acid mature region. The mature molecule of human MFG-E8 (i.e., Leu24-Cys387) is amino acids 24 through 387 of SEQ ID NO:2, which is herein referred to as SEQ ID NO:1.

SEQ ID NO:3—mouse MFG-E8—from GenBank NP032620 (This is the long form. Another splice form has 426 amino acids (NP001038954)):

```
  1    mqvsrvlaal  cgmllcasgl  faasgdfcds
       slclnggtcl  tgqdndiycl  cpegftglvc
 61    netergpcsp  npcyndakcl  vtldtqrgdi
       fteyicqcpv  gysgihcete  tnyynldgey
121    mfttavpnta  vptpaptpdl  snnlasrcst
       qlgmeggaia  dsqisasyvy  mgfmglqrwg
181    pelarlyrtg  ivnawhasny  dskpwiqvnl
       lrkmrvsgvm  tqgasragra  eylktfkvay
241    sldgrkfefi  qdesggdkef  lgnldnnslk
       vnmfnptlea  qyirlypvsc  hrgctlrfel
301    lgcelhgcle  plglknntip  dsqmsasssy
       ktwnlrafgw  yphlgrldnq  gkinawtaqs
361    nsakewlqvd  lgtqrqvtgi  itqgardfgh
       iqyvesykva  hsddgvqwtv  yeeqgsskvf
421    qgnldnnshk  knifekpfma  ryvrvlpvsw
       hnritlrlel  lgc.
```

Human MFG-E8 encoding DNA sequence minus the signal peptide (SEQ ID NO:4):

```
   1   ctggatatct gttccaaaaa ccctgccac
       aacgtggtt  tatgcgagga
  51   gatttcccaa gaagtgcgag gagatgtctt
       cccctcgtac acctgcacgt
 101   gccttaaggg ctacgcgggc aaccactgtg
       agacgaaatg tgtcgagcca
 151   ctgggcatgg agaatgggaa cattgccaac
       tcacagatcg ccgcctcatc
 201   tgtgcgtgtg accttcttgg gtttgcagca
       ttgggtcccg gagctggccc
 251   gcctgaaccg cgcaggcatg gtcaatgcct
       ggacacccag cagcaatgac
 301   gataacccct ggatccaggt gaacctgctg
       cggaggatgt gggtaacagg
 351   tgtggtgacg cagggtgcca gccgcttggc
       cagtcatgag tacctgaagg
 401   ccttcaaggt ggcctacagc cttaatggac
       acgaattcga tttcatccat
 451   gatgttaata aaaaacacaa ggagtttgtg
       ggtaactgga acaaaaacgc
 501   ggtgcatgtc aacctgtttg agaccccctgt
       ggaggctcag tacgtgagat
 551   tgtaccccac gagctgccac acggcctgca
       ctctgcgctt tgagctactg
 601   ggctgtgagc tgaacggatg cgccaatccc
       ctgggcctga agaataacag
 651   catccctgac aagcagatca cggcctccag
       cagctacaag acctggggct
 701   tgcatctctt cagctggaac ccctcctatg
       cacggctgga caagcagggc
 751   aacttcaacg cctgggttgc ggggagctac
       ggtaacgatc agtggctgca
 801   ggtggacctg ggctcctcga aggaggtgac
       aggcatcatc acccaggggg
 851   cccgtaactt tggctctgtc cagtttgtgg
       catcctacaa ggttgcctac
 901   agtaatgaca gtgcgaactg gactgagtac
       caggacccca ggactggcag
 951   cagtaagatc ttccctggca actgggacaa
       ccactccac  aagaagaact
1001   tgtttgagac gcccatcctg gctcgctatg
       tgcgcatcct gcctgtagcc
1051   tggcacaacc gcatcgccct cgcgcctggag
       ctgctgggct gttag.
```

MFG-E8 can be administered to the subject in a pharmaceutical composition comprising a pharmaceutically acceptable carrier. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution.

Compositions comprising MFG-E8 can be formulated without undue experimentation for administration to a subject, including humans, as appropriate for the particular application. Additionally, proper dosages of the compositions can be determined without undue experimentation using standard dose-response protocols.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compositions of the present invention can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the composition may also take place using a nasal tampon or nasal sponge.

The subject can be a human or another animal.

The present invention is directed to methods and compositions for treating radiation damage in a subject exposed to radiation above ambient levels or preventing radiation damage in a subject at risk for exposure to radiation above ambient levels. These effects are independent of the subject possibly having sepsis. Preferably, the subject does not have sepsis.

This invention will be better understood from the Experimental Details, which follow. However, one skilled in the art will readily appreciate that the specific methods and results discussed are merely illustrative of the invention as described more fully in the claims that follow thereafter.

Experimental Details

Introduction

The effect of recombinant human MFG-E8 (rhMFG-E8) in mortality and intestinal damage after exposure to high dose ionizing radiation was examined in Sprague-Dawley rats.

Materials and Methods

Experimental Animals.

Male Sprague-Dawley rats (250-350 g) purchased from Charles River Laboratories (Wilmington, Mass., USA) were used. The rats were housed in a temperature-controlled room on a 12-h light/dark cycle and fed on a standard Purina rat chow diet. Animal experimentation was carried out in accordance with the Guide for the Care and Use of Laboratory Animals. This project was approved by the Institutional Animal Care and Use Committee (IACUC) of the Feinstein Institute for Medical Research.

Animal Model of Whole Body Irradiation.

Rats were exposed to whole body irradiation (WBI) of either 7.5 or 10 Gray (Gy) using a Gammacell® 1000 Irradiator (Atomic Energy of Canada Ltd) [radiation source: Cesium-137 ($^{137}Cs$)]. The animals were sedated with intraperitoneal pentobarbital (40 mg/kg BW) prior to irradiation. During radiation, the container rotated continuously in front of the radiation source for even exposure. The animals were then returned to their cages, and food and water were provided. The lethal irradiation dose for 70% of the animals at 21 days ($LD_{70}/21$) was initially determined to be 10 Gy delivered at a dose rate of approximately 2.5 Gy/min for 4 min. Subsequent experiments were performed at a total radiation dose of 10 Gy.

Preparation and Administration of rhMFG-E8.

Human MGF-E8 is a 387 amino acid (aa) precursor that contains a 23 aa signal sequence and a 364 aa mature region (SwissProt # Q08431) was synthesized. The recombinant protein was greater than 99% pure, identified as human MFG-E8 with 95% confidence, and was rendered endotoxin free with Triton-X-114 treatment [15]. Rats were exposed to WBI as described above and randomly assigned to sham, treatment or vehicle groups. Animals in the treatment group received rhMFG-E8 (166 µg/kg BW) subcutaneously once a day with the first dose given 6 h after WBI. The animals received a total of 3 doses and were sacrificed 18 h after the last dose (or 72 h after WBI). In the Vehicle group, rhMFG-E8 was replaced with an equivalent volume of normal saline. All other parameters remained unchanged. Age and weight matched non-irradiated animals were used as sham-irradiated controls.

Survival Study.

To assess the survival benefits of rhMFG-E8, additional groups of animals were exposed to 10 Gy WBI and treated with rhMFG-E8 (166 µg/kg BW) subcutaneously once a day with the first dose given 6 h after WBI for 7 days and observed for 21 days, and the survival was recorded. The surviving animals beyond 21 days were then euthanized.

Histopathology.

Samples of the ileum from Sham, Vehicle and treatment groups from the 72 h time point were harvested 5 mm and 20 mm from the ileo-cecal junction. Four 2 mm sections from each animal were fixed in 1:10 buffered formalin and embedded in paraffin. Tissue blocks were sectioned at a thickness of 5 µm, transferred to glass slides, and stained with hematoxylin/eosin. The slides were examined with a Nikon Eclipse Ti inverted microscope, and intestinal injury was analyzed. A seven point scoring system, the radiation injury intestinal mucosal damage score (RIIMS, Range 7-32, Table 1), was developed by assessing changes in villus morphology, height and cell type composition, crypt cellular and nuclei appearance, lymph congestion and mucosal necrosis and exfoliation to grade the severity of damage. Computerized morphometric measurements were made with NIS-Elements BR laboratory image analysis system software. Villus length and crypt depth was measured in alternate villi using in 3-4 histological sections from each animal and measured. The number of enterocytes and goblet cells in neighboring villi were then counted under high magnification. Forty villi from 4 different parts of each sample slide were sequentially chosen and the average counts were utilized. Histology of the ileal tissue from 4 different animals were analyzed in each group.

Western Immunoblotting.

Ileal tissue lysates (80-100 µg) were electrophoresed on NuPAGE 4-12% Bis-Tris gels and transferred to 0.2 µm nitrocellulose membrane (Invitrogen, Carlsbad, Calif.). The membranes were blocked in TBS-T (10 mM Tris-HCl, 150 mM NaCl, 0.1% Tween-20) containing 5% non-fat milk for 1 h at room temperature. Western blotting was performed using the following primary antibodies: rabbit anti-p21 antibody (C-19) and rabbit anti-Bcl-2 polyclonal antibody (N-19) (1:1000) (Santa Cruz Biotechnology). After incubation of the primary antibodies overnight at 4° C., the membranes were washed with TBS-T. Immunoreactive bands were detected using HRP-linked anti-rabbit IgG (1:10,000) (Southern Biotech, Birmingham, Ala.) and the Enhanced Chemiluminescence (ECL) Western blot detection kit (Amersham, Piscataway, N. J.). The immunoblots were exposed to X-ray film and analyzed with the NIH ImageJ analysis system. Mouse anti-β-actin monoclonal antibody (1:20,000) (Sigma) was used as a loading control in all Western blot experiments.

Total RNA Extraction and Real Time PCR.

Total RNA was extracted from the ileum by Tri-Reagent (Molecular Research Center, Cincinnati, Ohio). RNA (5 µg) from each sample was reverse-transcribed in a 20 µl reaction volume containing 50 mM KCl, 10 mM Tris-HCl, 5 mM $MgCl_2$, 1 mM dNTP, 20 U RNase inhibitor, 2.5 mM oligo $(T)_{16}$ primer, and 50 U reverse transcription. The reverse transcription reaction solution was incubated at 42° C. for 1 hour, followed by heating at 95° C. for 5 minutes; 1 µl cDNA was amplified with 0.15 µM each of 3' and 5' primers specific for rat p53 and p21. Rat glyceraldehyde 3-phosphate dehydrogenase (G3PDH) was used as the housekeeping gene. The primers are as follows: 5'-TGA GGA ACA AGG AAC CAG-3' (forward) (SEQ ID NO:5) and 5'-GGA AGG ACA CGC ACA TAG-3' (reverse) (SEQ ID NO:6) for MFG-E8,5'-CCC CAC CGC CTG TAA GAT T-3' (forward) (SEQ ID NO:7) and 5'-ATG GGT CCG GAG GAT ACA GAT-3' (reverse) (SEQ ID NO:8) for p53 (NM_030989), 5'-CGG GAC CGG GAC ATC TC-3' (forward) (SEQ ID NO:9) and 5'-CGG CGC TTG GAG TGA TAG AA-3' (reverse) (SEQ ID NO:10) for p21 (U24174), and 5'-TGA AGG TCG GTG TCA ACG GAT TTG GC-3' (forward) (SEQ ID NO:11) and 5'-CAT GTA GGC CAT GAG GTC CAC CAC-3' (reverse) (SEQ ID NO:12) for G3PDH (M17701). Each cycle consisted of 30 seconds at 94° C., 30 seconds at 60° C., and 45 seconds at 72° C.

Irradiation of Intestinal Epithelial Cells (IEC-6) and MFG-E8 Treatment.

Rat small intestinal cell line, IEC-6 cells were obtained from American Type Culture Collection (ATCC), were cultured in DMEM media (Invitrogen) with 10% FBS, penicillin and streptomycin, and kept in 37° C. incubator under humidified conditions containing 5% $CO_2$. Cells were plated in 96-well plates overnight and irradiated at 8 Gy using an X-ray irradiator (RS-2000 Biological Irradiator, Rad Source). In some wells, the cells were treated with rhMFG-E8 (0.5 µg/ml) 1 h prior to and immediately after irradiation. Cells were stained with crystal violet at 48 h after treatment for analysis.

Statistical Analysis.

All data are expressed as mean±SE and analyzed by one way analysis of variance (ANOVA) and compared using Student Newman Keuls test. The survival curves were plotted using the Kaplan-Meier Analysis, and the curves were subjected to the Log Rank test. The differences in values were considered significant if $p<0.05$.

Results rhMFG-E8 Improves Survival after Whole Body Irradiation (WBI).

High dose WBI is associated with high mortality. The $LD_{70}/21$ of acute WBI for the present experimental cohort (healthy adult male Sprague-Dawley rats) was determined to be 10 Gy (FIG. 1A). To determine the beneficial effects of rhMFG-E8, rhMFG-E8 (166 µg/kg BW) was administered subcutaneously once a day for 7 days. The first dose was given 6 h after WBI. Animals were allowed standard Purina chow and water ad libitum and observed over 21 days. The mortality rate was compared to that of WBI rats treated with equivalent volumes of normal saline given subcutaneously. Treatment with rhMFGE-8 dramatically improved the survival in WBI rats from 31% to 75% (FIG. 1B).

Figure 2:
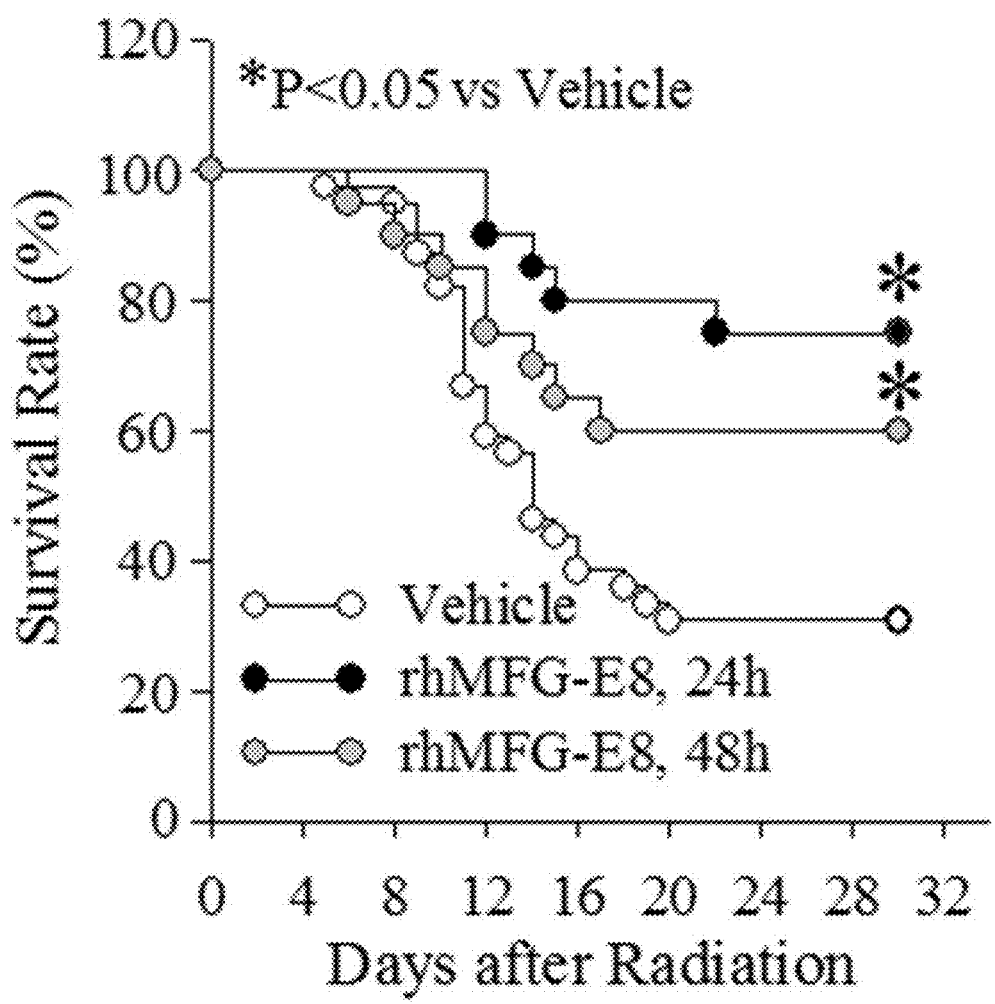
FIG. 2. Administration of rhMFG-E8 at 24 hours or 48 hours after exposure to WBI (10-Gy) improved survival rate from 30% to 75% post-24 h (p=0.001) and to 60% post-48 h (p=0.05) at 30 days after WBI (n=20/group).

To test whether further delayed administration of rhMFG-E8 also produces the survival benefit, rhMFG-E8 (~150 µg/kg BW) was administered subcutaneously once a day for 7 days with the first dose given at either 24 h or 48 h post-WBI (10-Gy). As shown in FIG. 2, further delayed administration of rhMFG-E8 improved survival rate from 30% to 75% post-24 h (p=0.001) and to 60% post-48 h (p=0.05) at 30 days after WBI (n=20/group). Thus, rhMFG-E8 is an effective post-exposure mitigator of acute radiation injury.

Post-Exposure Administration of rhMFG-E8 Prevents Body Weight (BW) Loss after WBI.

BW was recorded daily in the 30-day survival study. There is a clear distinction in BW between survivors and non-survivors throughout in vehicle and rhMFG-E8-treated animals (FIG. 3A-B, each rat depicted in a single line). During the initial 5 days after irradiation, BW loss was similar between two groups. After day 8, the rats in the vehicle group (FIG. 3A) continued to lose weight and died while majority animals in the rhMFG-E8-treated group (FIG. 3B) showed consistent gain in BW and survived.

In a separate cohort, after irradiation and treatment, the animals were kept in metabolic cages. The food intake, stool weight, water intake and urine output were measured for 7 days. The results showed that average stool weight was lower in the MFG-E8 treated rats as compared to vehicle group which was indicative of diarrhea or loose stool in the vehicle group as opposed to normal stool in the MFG-E8 treated rats. No major changes were observed in all other parameters studied.

rhMFG-E8 Preserves Intestinal Structure and Function after WBI.

Figures 4A, 4B, 4C:
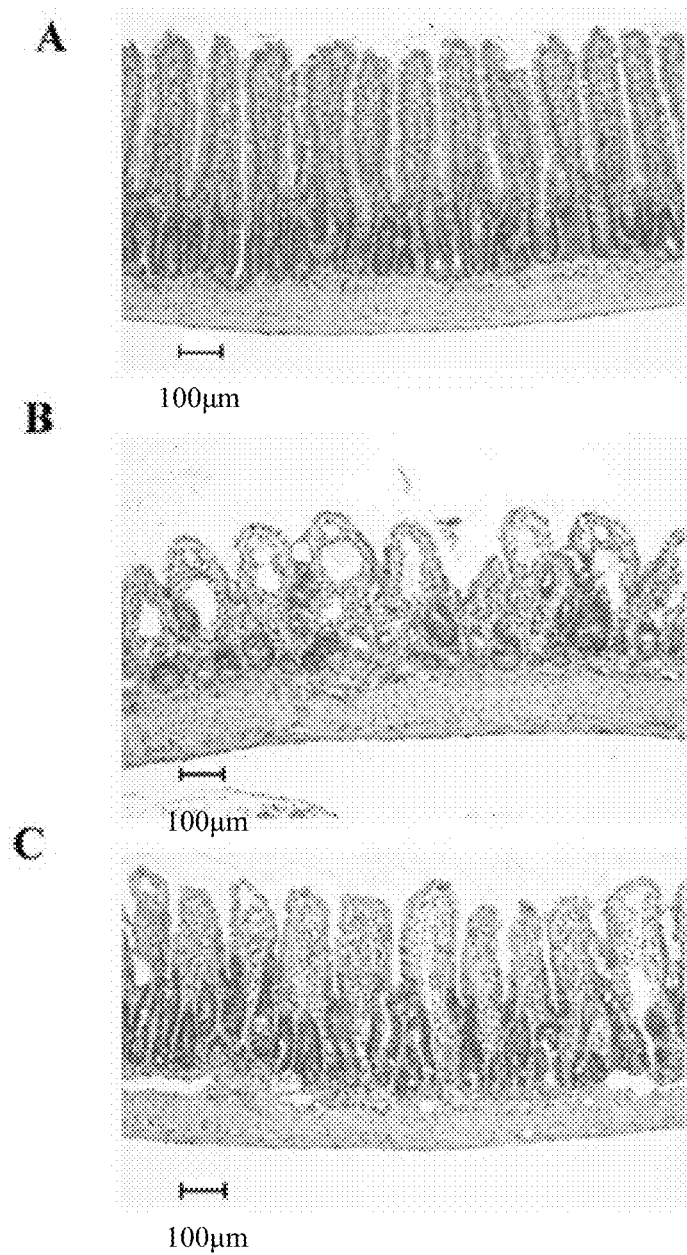
FIG. 4A-4C. Histology of rat ileum 72 h after WBI. Histological sections of the rat ileum from non-irradiated (sham) animals (A), Vehicle (B) and rhMFG-E8 treated animals (C) harvested 72 h after WBI (×20 magnification).
Figures 5A, 5B, 5C:
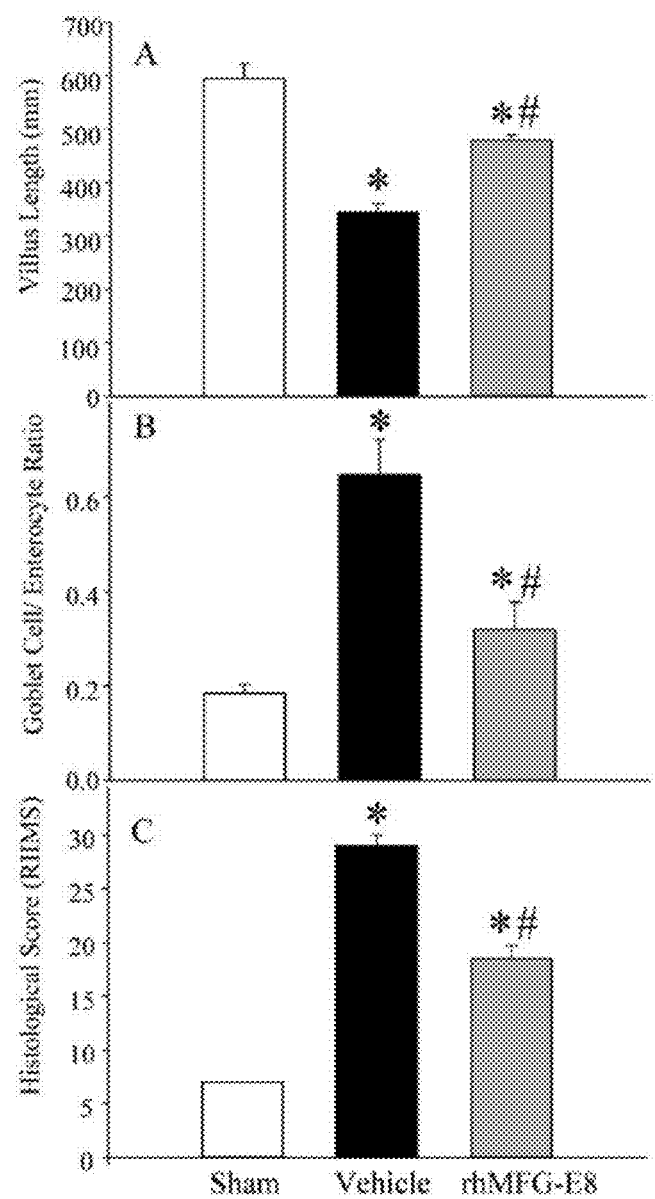
FIG. 5A-5C. Morphometric histological measurements. Computerized morphometric measurements were made with NIS-Elements BR laboratory image analysis system software. Comparison of mean villus length (A), Goblet cell/enterocyte ratio (B) and the radiation injury intestinal mucosal damage score (RIIMS) (C) were analyzed. Data are presented as mean±SE (n=4) and compared with Student Neuman Keuls test by ANOVA. * P<0.05 vs. Sham; # P<0.05 vs. Vehicle.

To determine the effect of WBI on gut morphology and function, hematoxylin and eosin (H&E) stained sections of the gut were examined with light microscopy (FIG. 4). At 72 h after WBI, ileal sections showed extensive mucosal damage (FIG. 4B). There was severe widespread denudation and altered morphology of the crypts and villi, reparative changes with an increase in cryptogenic activity and abnormal mitotic activity, mucosal necrosis and ulceration. Treatment with rhMFG-E8 resulted in an improvement in histological appearance: there was preservation of villus height and form, and preservation of mucosal layer integrity (FIG. 4C). The villus length in the vehicle group was reduced by 42% from the control group, compared to a significantly smaller 19% reduction seen with rhMFG-E8 treatment (FIG. 5A). In addition, there was a reduction in the number of nutrient absorbing enterocytes in surviving villi in the vehicle group reflected in an increase in the Goblet cell/enterocyte ratio, which was significantly reduced in the treatment group (FIG. 5B). These findings are consistent with the gastrointestinal findings observed in acute radiation syndrome. Based on these and other parameters, a seven point scoring system, the radiation injury intestinal mucosal damage score (RIIMS, range 7-32), was developed to grade the severity of damage (Table 1). The parameters assessed were: goblet cell/enterocyte ratio, villus length as a percentage of normal (sham), villus shape/morphology, crypt cellularity/regeneration, crypt nuclei appearance, Lymph congestion and mucosal necrosis/exfoliation. There was a significant 36% reduction in the RIIMS score in rhMFG-E8 treated rats compared to vehicle treated irradiated animals. rhMFG-E8 treated rats had a score of 18.5±2.4 from a maximum score of 32, compared to vehicle treated rats with a score of 29±2 (Table 2, FIG. 5C).

rhMFG-E8 Attenuates the Increased Gut Permeability and Endotoxemia Induced by WBI.

Translocation of intestinal bacteria can occur during GI tract damage, leading to lethality. To determine the effect of rhMFG-E8 on gut permeability, the ileal segments were harvested from WBI rats at day 9 post-exposure and subjected to in vivo gut permeability assay using FITC-dextran. As shown in FIG. 6A, gut permeability in the vehicle group was 5.3-fold higher than the sham, while rhMFG-E8 administered 24 h post-exposure for 7 days resulted in a 29% reduction. In addition, the mesenteric lymph nodes harvested from the sham, vehicle, and rhMFG-E8-treated rats were homogenized and cultured for bacteria. The vehicle group had significantly higher bacterial count than the sham, while rhMFG-E8 group had a much lower bacterial count than the vehicle group (FIG. 6B). Correspondingly, serum endotoxin levels, measured by *Limulus Amebocyte* Lysate method, in vehicle group were 4.1-fold higher than the sham, while its levels in the rhMFG-E8-treated animals were comparable to the sham (FIG. 6C).

MFG-E8 Gene Expression is Altered after WBI.

Figure 7:
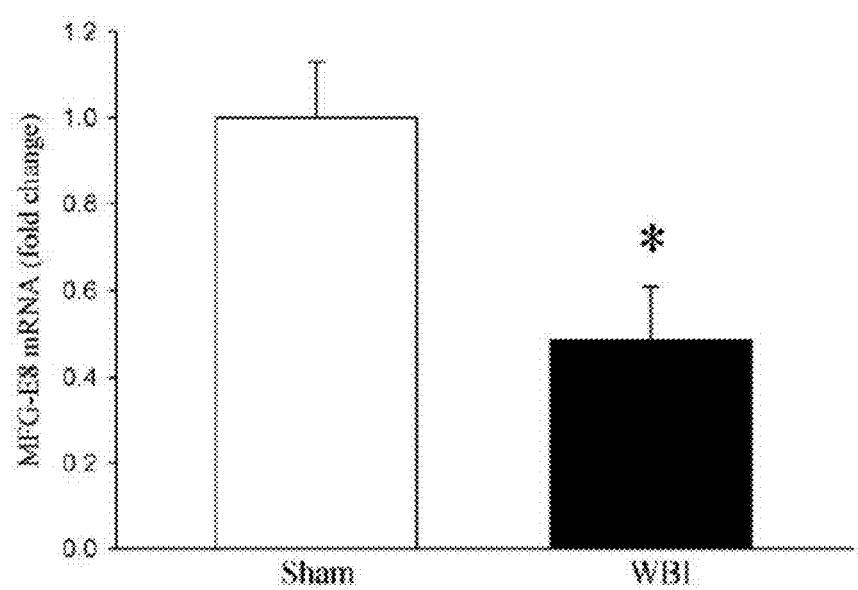
FIG. 7. MFG-E8 gene expression in the intestine. Total RNA from gut tissues of Sham and WBI animals was extracted and reverse transcribed. The mRNA expression of MFG-E8 was determined by real-time PCR and fold change over GAPDH is shown. Data are presented as mean±SE (n=3-4) and compared by Student's-t-test. *P<0.05 vs. Sham.

To examine whether WBI-induced gut injury is associated with alterations of intestinal MFG-E8 gene expression, ileal tissue from sham and WBI-treated animals for 72 h were measured for MFG-E8 gene expression. A significant 51% decrease in MFG-E8 gene expression was observed in WBI-treated animals as compared to sham controls (FIG. 7). These data suggest that decrease in intestinal MFG-E8 may contribute to WBI-treated intestinal injury and mortality.

rhMFG-E8 Upregulates p53 Expression and Increases p21 after WBI.

Figures 8A, 8B, 8C:
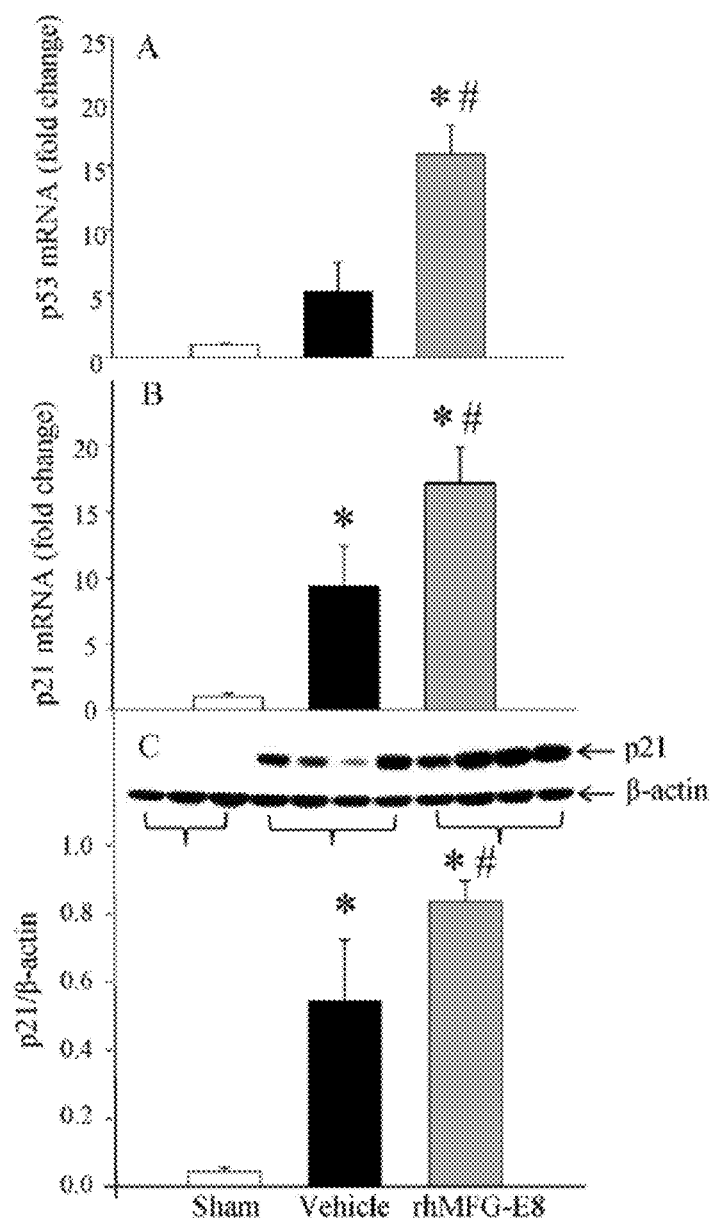
FIG. 8A-8C. Analysis of cell cycle regulators. Total RNA from gut tissues of Sham, Vehicle and rhMFG-E8 treated animals was extracted and reverse transcribed. The mRNA expression of the cell cycle regulators p53 (A) and p21 (B) were determined by real time PCR and fold change over GAPDH is shown. Proteins were extracted and subjected to Western blotting using p21 and β-actin antibody. A representative blot is shown and the ratio between p21 and β-actin was calculated and plotted (C). Data are presented as mean±SE (n=6-8) and compared with Student Neuman Keuls test by ANOVA. *P<0.05 vs. Sham; # P<0.05 vs. Vehicle.

The severity of the GI syndrome is directly correlated to the loss of functional epithelium. Ionizing radiation is a potent cause of apoptosis and several studies have shown an increase in apoptotic activity following GI irradiation. A larger proportion of cell death is however due to catastrophic mitotic activity. It involves cell death occurring either during or shortly after dysregulated mitosis in cells with damaged DNA [16,17]. The regulatory protein p53, is a tumor suppressor protein which is situated at the crossroads of a network of signaling pathways that are essential for cell growth regulation and apoptosis [18,19]. As illustrated in FIG. 7, analysis of the ileum after WBI showed a 416% increase of p53 expression in vehicle treated animals. Treatment with rhMFG-E8 significantly magnified this response with a 15-fold increase from the control group (FIG. 8A). The downstream effector gene p21 increased accordingly with an 8-fold increase in the vehicle group compared to a 16-fold increase after rhMFG-E8 administration (FIG. 8B). Similarly, there was a corresponding increase of 13-fold in p21 protein levels in the vehicle group compared to 20-fold increase after rhMFG-E8 treatment.

rhMFG-E8 Increases Bcl-2 in Ileal Mucosa after WBI.

Figure 9:
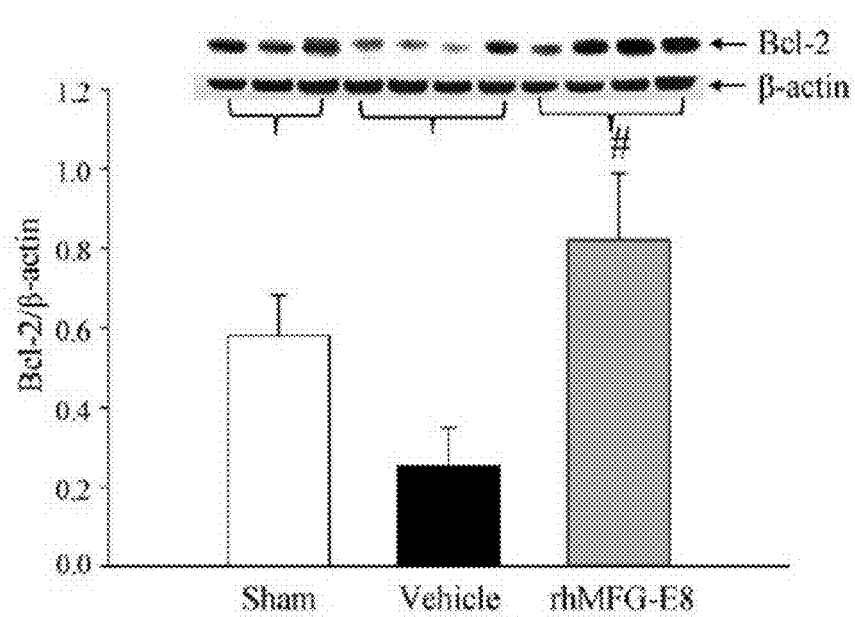
FIG. 9. Changes in Bcl-2. Proteins from gut tissues were electrophoresed and Western blotted with bcl-2 and β-actin antibody. A representative blot is shown and the ratio between bcl-2 and β-actin was calculated and plotted. Data are presented as mean±SE (n=6-8) and compared with Student Neuman Keuls test by ANOVA. # P<0.05 vs. Vehicle.

To determine the effects of rhMFG-E8 on WBI induced apoptosis, the levels of the anti-apoptotic protein Bcl-2 were determined in the ileum. There was a 43% decrease in Bcl-2 levels in the vehicle group from the sham group as compared to a 41% increase in rhMFG-E8 treated animals (FIG. 9). This represented a 141% increase from the vehicle treated animals. The significant difference in the Bcl-2 levels between the vehicle and treatment groups correlates positively with the improved outcomes that we observed in the rhMFG-E8 treated rats.

rhMFG-E8 Protects IEC-6 Cells from Radiation-Induced Cell Death.

Figure 10:
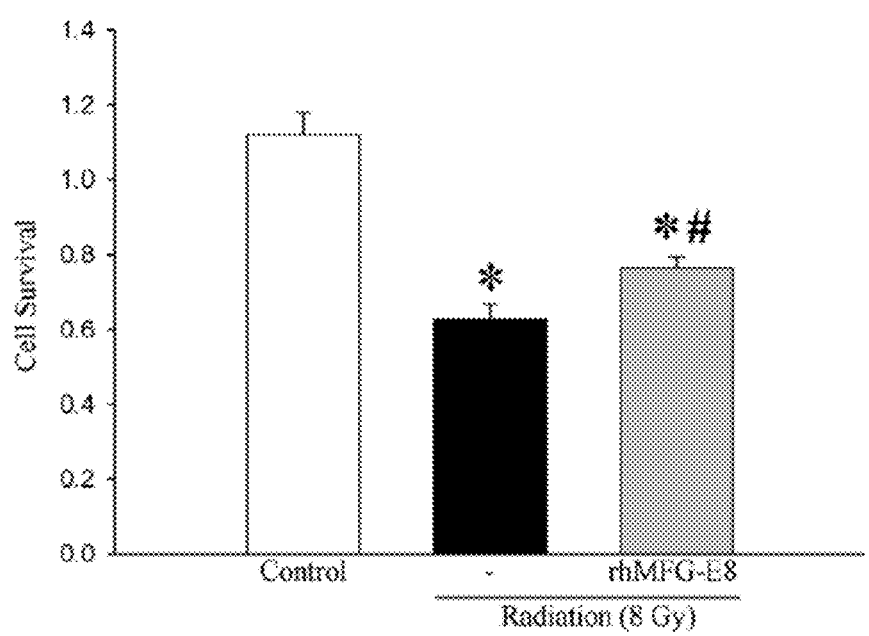
FIG. 10. Assessment of cell death. Intestinal epithelial cells (IEC-6) were irradiated at 8 Gy, treated with rhMFG-E8 (0.5 µg/ml) 1 h prior to and immediately after irradiation, and stained with crystal violet. Data are presented as mean±SE (n=7) and compared with Student Neuman Keuls test by ANOVA. *P<0.05 vs. Control; #P<0.05 vs. Vehicle.

To determine if intestinal epithelial cells are sensitive to MFG-E8-mediated protection, IEC-6 cells were irradiated at 8 Gy, untreated or pre-treated with 0.5 μg/ml MFG-E8, and stained with crystal violet. Cells treated with 8 Gy showed significant decrease in cell survival as compared to untreated cells. MFG-E8 treatment prior to 1 h followed by immediately after irradiation showed higher staining with crystal violet indicative of protection from cell death (FIG. 10). Although indirect, these studies indicated that intestinal epithelial cells could be at least one cell type that MFG-E8 would be able to either protect or possibly restore after irradiation of the intestinal tissues.

Discussion

Ionizing radiation is widely used in medicine and industry. It is utilized in radiotherapy and nuclear imaging for the diagnosis, treatment and monitoring of cancers; in industry for non-destructive testing, in gauges, as radioactive tracers and in the generation of electrical power in nuclear reactors/power plants. Recent world events have highlighted the continuing dangers associated with the utilization of nuclear power. Although nuclear energy is clean and sustainable, it can cause enormous damage in adverse conditions and as illustrated by the Tōhoku earthquake and tsunami and the consequent massive radiation leak at the Fukushima I and other power plants, the risk of radiation exposure cannot be completely eradicated even with the most stringent measures. Ionizing radiation causes various lesions by direct interaction with DNA and indirectly through damage produced by free radicals. After DNA damage has occurred, a number of processes occur in the damaged cell which are important for recovery after radiation exposure but may also play a role in the development of toxicity. Activation of DNA repair, expression of radiation response genes, stimulation of proliferation, and initiation and perpetuation of inflammation could ultimately result in self-perpetuating cascades that lead to vascular damage, tissue hypoxia, widespread cellular dysfunction and death. A probable mechanism for a successful mitigator of radiation injury would be to target these pathways to prevent or reduce toxicity [1,20].

The amount of damage caused by ionizing radiation is dependent on the dose rate of the radiation and the sensitivity of the organism being irradiated. Therefore, a determination was made of the sensitivity of the experimental cohort, male Sprague-Dawley rats using a Gammacell® 1000 Irradiator (Atomic Energy of Canada Ltd), which utilizes Cesium-137 ($^{137}$Cs) as a gamma (γ) rays emitting radiation source. Small amounts of $^{137}$Cs and $^{134}$Cs are released into the environment during nearly all nuclear weapon tests and some nuclear accidents, most notably the Chernobyl disaster. It has also been found in the plumes emanating from the continuing leakage at the Fukushima reactors in Japan. A WBI dose of 10 Gy was lethal to 70% of the population of male Sprague-Dawley rats by 21 days ($LD_{70}/21$) (FIG. 1A), with the first deaths occurring by Day 7. This corresponds to damage from severe radiation and indicates that the GI syndrome component of ARS was a major contributor to mortality. In this study with 10 Gy, 70% mortality was observed within 15 days, and the mortality remained the same for an additional week. Therefore, in the treatment study, animals were only observed for 21 days. Treatment of irradiated rats with rhMFG-E8 (166 µg/kg BW) subcutaneously once a day for 7 days produced significant survival benefits. This was observed as early as day 14 (2-fold increase in survival, p=0.018) and remained till the end of the observation period by day 21 with a 142% increase in survival (p=0.027). The survival advantage observed compares favorably even with interventions given in tested animals before irradiation. This was especially remarkable as the survival benefits persisted for over 2 weeks after treatment had been stopped. In addition, a strong correlation exists between body weight changes and survival after WBI.

rhMFG-E8 was used rather than the rodent-derived protein because of its increased translational potential and reduced likelihood of antigenicity in humans. Further, being a recombinant protein, it offers distinct cost advantages for future mass production. It was determined that subcutaneous administration as opposed to an intravenous route would provide a quick route of administration in the event of a nuclear disaster without the need for specialized personnel. Thus, rhMFG-E8 is in a unique niche as a strong candidate for clinical use as a radio-mitigator.

MFG-E8 is a glycoprotein that is comprised of a cleavable signal peptide, followed by two N-terminal EGF-like repeats and two C-terminal Discoidin/F5/8C domains (referred to as F5/8C domains). The arginine-glycine-aspartic acid (RGD) integrin-binding motif on its second EGF domain engages αvβ3/5 integrin heterodimers to facilitate cell adhesion and induce integrin-mediated signal transduction. Each F5/8C domain is composed of an eight-strand anti-parallel β-barrel. Two or three hypervariable loops extend from these and mediate binding to carbohydrate moieties on the surface of cells and in the extracellular matrix. The second C-terminal domain of MFG-E8 also binds to anionic phospholipids of cellular membranes [9,11,21-23]. MFG-E8 is a potent opsonin for the clearance of apoptotic cells. It is produced by mononuclear cells of immune-competent organs including the spleen and the liver. MFG-E8 facilitates a myriad of inter-cellular interactions, including the maintenance of the intestinal epithelium. Cell proliferation, differentiation, and migration are crucial events required for the maintenance of an intact epithelial layer. Bu et al demonstrated that MFG-E8 promotes the migration of intestinal epithelial cells through reorientation of the actin cytoskeleton and that in septic mice, depleting MFG-E8 interrupted enterocyte migration, impaired restitution impeded mucosal healing [12]. MFG-E8 has also been shown to be beneficial in colitis and other forms of intestinal damage [7,13,14]. These data indicate that MFG-E8 plays an important role in the maintenance of intestinal epithelial homeostasis and the promotion of mucosal healing, essential attributes in its mitigation of GI impairment after WBI.

The full ARS GI syndrome ensues with acute doses of 10 Gy or more, although symptoms may occur as low as 6 Gy. Histological changes include the loss of intestinal crypt cells and breakdown of the mucosal barrier, with sloughing of the epithelial cell layer and denudation of the bowel wall. Impaired barrier function of the gastrointestinal tract results in dehydration, electrolyte imbalance and increased passage of bacteria and their toxins through the intestinal wall into the bloodstream, predisposing to infection and sepsis. Other severe complications include ulceration and necrosis of the bowel wall, leading to stenosis, ileus, and perforation. Recovery is unlikely, as the radiosensitive stem cells in the crypts of the gastrointestinal tract are permanently damaged. Survival is extremely improbable with this syndrome and death usually occurs within 2 weeks. The histology of the small intestine 72 h after WBI (FIG. 4) highlights these morphological changes. These changes were attenuated by treatment with rhMFG-E8: histological sections showed conservation of the normal villus structure and increased cryptogenic height and activity pointing to replacement of damaged cells. It is pertinent to also note the paucity of abnormal mitotic nuclei in the crypt after rhMFG-E8 treatment when compared to the Vehicle group. This positive effect of rhMFG-E8 on the gut after WBI irradiation is due, at least in part to its ability to repair damaged intestinal epithelium and preserve gut homeostasis [12].

The ileo jejunum region of the GI tract has been shown to be particularly sensitive to acute radiation damage. Additionally damage to this portion of the small intestine leads to malabsorption and malnutrition—an important systemic effect that worsens morbidity and reduces chances of recovery. Hence the ileum was chosen as a representative segment of the small intestine to study the effects of rhMFG-E8 after WBI [24]. Data from the histological sections indicate that MFG-E8 is able to restore the integrity of the ileum after WBI.

Hematopoietic parameters such as white blood cell count, red blood cell count, hemoglobin, hematocrit, and platelet count were also assessed at 20 h and one week after WBI. With the exception of the white blood cell count, all measurements were similar to sham levels. The white blood cell count dramatically decreased as early as 20 h and the treatment with MFG-E8 slightly improved the count, but was not significant. Recent unpublished observations from the lab suggests that in animals that survived for 30 days after WBI the white blood cell count returned back to sham levels.

A further mechanism by which rhMFG-E8 confers a therapeutic advantage after WBI is by upregulating p53. First described in 1979, p53 is a tumor suppressor protein that acts as a regulator of the cell cycle. It is situated at the crossroads of a network of signaling pathways that are essential for cell growth regulation and apoptosis [18,19, 25-28]. In normal unstressed cells, the low levels of p53 protein are maintained as p53 binds to MDM2 and other negative regulators. This promotes its degradation via the ubiquitin/proteasome pathway. After genotoxic stresses, p53 levels accumulate in the cell through the inhibition of its interaction with negative regulators [28-30]. Activated p53 binds DNA and activates expression of p21/waf1/cip1 gene which encodes p21, a member of the Cip/Kip family of cyclin-dependent kinase (CDK) inhibitors. The importance of p53 function after irradiation was demonstrated by Kirsch et al. [16]. They found that selective deletion of p53 from the GI epithelium sensitized irradiated mice to the GI syndrome and that transgenic mice with overexpression of p53 in all tissues were protected from the GI syndrome after irradiation, a finding corroborated by another study [16,31]. Treatment with rhMFG-E8 led to an increased expression in the gut of p21, which is known to be critical to cell survival after genotoxic insults [32,33]. Moreover, Komarova et al showed that p21-null animals had accelerated development of lethal GI syndrome after 15Gy gamma irradiation and suggested that the protective role of p53 in ionizing radiation-induced GI syndrome is mediated by p21 [31]. By increasing p53 and p21, major regulators of the cell cycle, rhMFG-E8 improves cell survival and protects the genome.

The present results demonstrate that treatment with rhMFG-E8 after WBI upregulates gut Bcl-2. Bcl-2 is an anti-apoptotic protein located on the outer mitochondrial membrane, which inhibits caspase activity by preventing the release of cytochrome c from the mitochondria and by binding to the apoptosis-activating factor (APAF-1) [34-36]. The observed increase in Bcl-2 suggests that rhMFG-E8 treatment also acts to prevent apoptotic cell death after WBI. Taken together, these findings reveal that rhMFG-E8 working through various signaling pathways confers a considerable survival advantage when administered several hours after WBI.

MFG-E8 has previously been shown to exert its beneficial effects in sepsis by increasing apoptotic cell clearance and producing anti-inflammatory properties [37,38]. It is well recognized that MFG-E8 binds to $\alpha_v\beta_3/\alpha_v\beta_5$ integrin [39]. Recently, another direct mechanism of MFG-E8 was elucidated in mediating anti-inflammation. MFG-E8 inhibits LPS-induced TNF-α production via SOCS3 dependent downregulation of NF-κB [40]. However, the precise mechanism of MFG-E8 mediated protection of intestinal tissue after WBI has not been elucidated. One possibility is that MFG-E8-induced p53/p21 upregulation leads to cell cycle arrest in the G1 phase and prevents cells from inappropriately entering into mitosis after WBI. A second scenario is that MFG-E8-mediated p53/p21 upregulation inhibits intestinal tissue apoptosis and thus preserves tissue integrity. In that regard, Bcl-2, an anti-apoptotic marker, was significantly increased in the rat ileum of MFG-E8 treated animals while its expression was diminished in the vehicle group.

The ongoing possibility of an unexpected nuclear catastrophe necessitates the development of viable mitigators of acute large dose radiation injury. The prevalent cause of death following higher doses of radiation is the GI syndrome component of ARS, which occurs even after rescue by bone marrow replacement. The present studies demonstrate that rhMFG-E8 given 6 hour after WBI significantly improved survival and ameliorated the GI syndrome. This survival advantage could involve additional body systems. Given its dramatic effect on outcome after WBI, rhMFG-E8 likely reduces the long term complications seen after WBI. rhMFG-E8 upregulates p53 and p21 after WBI. While increased p53 has been noted to have different outcomes in various studies, the dramatic improvement in survival with which it is associated in this study points to a unique interaction with rhMFG-E8 to improve cell survival while preserving function [16,25,31,41].

TABLE 1

The radiation injury intestinal mucosal damage score (RIIMS).

A. Increase in goblet cells

1. No increase in goblet cell number (defined by goblet cell/enterocyte ratio) (+/−10% of sham average)
2. >10-25% increase or >10%-100% decrease
3. >25-50% increase or >100% decrease
4. >50-100% increase
5. >100-200% increase
6. >200% increase B. Villus Length: Villus length as a percentage of normal (sham)

1. Normal length (−5 to + 10%)
2. 5-10% shortening or ≥10% increase in length
3. >10-20% shortening
4. >20-30% shortening
5. >30-40% shortening
6. >40% shortening C. Villus shape/morphology 1. Normal morphology
2. Mild abnormalities
3. Forked, fused villi
4. Flattening, loss of finger-like projections D. Crypt cellularity/regeneration 1. Normal crypt cellularity
2. Mild hypo/hypercellularity
3. Marked reparative/inflammatory changes
4. Abnormal crypt regeneration/ Marked crypt hypocellularity E. Crypt nuclei appearance 1. Normal nuclear appearance
2. Mild nuclear atypia/increased mitosis
3. Moderate nuclei atypia
4. Severe nuclear abnormalities F. Lymph congestion 1. No central villus lymph vessel congestion
2. Mild
3. Moderate
4. Severe TABLE 1-continued The radiation injury intestinal mucosal damage score (RIIMS).

G. Mucosal Necrosis/exfoliation

1. Normal brush border
2. Mild exfoliation brush border
3. Loss of brush border with mild exfoliation
4. Superficial ulcers RIIMS is a seven point scoring assessing changes in villus morphology, height and cell type composition, crypt cellular and nuclei appearance, lymph congestion and mucosal necrosis and exfoliation to grade the severity of damage. Scores range from 1-6. The minimum collated score of 7 corresponds to normal mucosa with a maximum score of 32 indicating the worst possible damage.

TABLE 2

RIIMS score at 72 h after WBI. Histological sections of ileum from Sham, Vehicle and rhMFG-E8 treated animals were scored by criteria described in Table 1.

| Histological parameter | Sham | Vehicle | rhMFG-E8 |
|---|---|---|---|
| Increase in goblet cell | 1 | 5.75 | 3.5 |
| Change in villus length | 1 | 5.5 | 3.25 |
| Villus shape/morphology | 1 | 3.5 | 2.5 |
| Crypt cellularity/regeneration | 1 | 3.5 | 2.25 |
| Crypt nuclei appearance | 1 | 3.5 | 2.25 |
| Lymph congestion | 1 | 3.75 | 2.5 |
| Mucosal necrosis/exfoliation | 1 | 3.5 | 2.25 |
| Total score | 7 | 29 | 18 |

REFERENCES

1. Citrin D, Cotrim A P, Hyodo F, Baum B J, Krishna M C, et al. (2010) Radioprotectors and mitigators of radiation-induced normal tissue injury. Oncologist 15: 360-371.
2. Kouvaris J R, Kouloulias V E, Vlahos L J (2007) Amifostine: the first selective-target and broad-spectrum radioprotector. Oncologist 12: 738-747.
3. Singh V K, Yadav V S (2005) Role of cytokines and growth factors in radioprotection. Exp Mol Pathol 78: 156-169.
4. Waselenko J K, MacVittie T J, Blakely W F, Pesik N, Wiley A L, et al. (2004) Medical management of the acute radiation syndrome: recommendations of the Strategic National Stockpile Radiation Working Group. Ann Intern Med 140: 1037-1051.
5. Wolbarst A B, Wiley A L, Jr., Nemhauser J B, Christensen D M, Hendee W R (2010) Medical response to a major radiologic emergency: a primer for medical and public health practitioners. Radiology 254: 660-677.
6. Stubbs J D, Lekutis C, Singer K L, Bui A, Yuzuki D, et al. (1990) cDNA cloning of a mouse mammary epithelial cell surface protein reveals the existence of epidermal growth factor-like domains linked to factor VIII-like sequences. Proc Natl Acad Sci USA 87: 8417-8421.
7. Aziz M M, Ishihara S, Mishima Y, Oshima N, Moriyama I, et al. (2009) MFG-E8 attenuates intestinal inflammation in murine experimental colitis by modulating osteopontin-dependent alphavbeta3 integrin signaling. J Immunol 182: 7222-7232.
8. Matsuda A, Jacob A, Wu R, Zhou M, Nicastro J M, et al. (2011) Milk fat globule-EGF factor VIII in sepsis and ischemia-reperfusion injury. Mol Med 17: 126-133.
9. Couto J R, Taylor M R, Godwin S G, Ceriani R L, Peterson J A (1996) Cloning and sequence analysis of human breast epithelial antigen BA46 reveals an RGD cell adhesion sequence presented on an epidermal growth factor-like domain. DNA Cell Biol 15: 281-286.
10. Hvarregaard J, Andersen M H, Berglund L, Rasmussen J T, Petersen T E (1996) Characterization of glycoprotein PAS-6/7 from membranes of bovine milk fat globules. Eur J Biochem 240: 628-636.
11. Raymond A, Ensslin M A, Shur B D (2009) SED1/MFG-E8: a bi-motif protein that orchestrates diverse cellular interactions. J Cell Biochem 106: 957-966.
12. Bu H F, Zuo X L, Wang X, Ensslin M A, Koti V, et al. (2007) Milk fat globule-EGF factor 8/lactadherin plays a crucial role in maintenance and repair of murine intestinal epithelium. J Clin Invest 117: 3673-3683.
13. Chogle A, Bu H F, Wang X, Brown J B, Chou P M, et al. (2011) Milk fat globule-EGF factor 8 is a critical protein for healing of dextran sodium sulfate-induced acute colitis in mice. Mol Med 17: 502-507.
14. Cui T, Miksa M, Wu R, Komura H, Zhou M, et al. (2010) Milk fat globule epidermal growth factor 8 attenuates acute lung injury in mice after intestinal ischemia and reperfusion. Am J Respir Crit Care Med 181: 238-246.
15. Qiang X, Li J, Wu R, Ji Y, Chaung W, et al. (2011) Expression and characterization of recombinant human milk fat globule-EGF Factor VIII. Int J Mol Med 28: 1071-1076.
16. Kirsch D G, Santiago P M, di Tomaso E, Sullivan J M, Hou W S, et al. (2010) p53 controls radiation-induced gastrointestinal syndrome in mice independent of apoptosis. Science 327: 593-596.
17. Kroemer G, Galluzzi L, Vandenabeele P, Abrams J, Alnemri E S, et al. (2009) Classification of cell death: recommendations of the Nomenclature Committee on Cell Death 2009. Cell Death Differ 16: 3-11.
18. Goldstein I, Marcel V, Olivier M, Oren M, Rotter V, et al. (2011) Understanding wild-type and mutant p53 activities in human cancer: new landmarks on the way to targeted therapies. Cancer Gene Ther 18: 2-11.
19. Horn H F, Vousden K H (2007) Coping with stress: multiple ways to activate p53. Oncogene 26: 1306-1316.
20. Bentzen S M (2006) Preventing or reducing late side effects of radiation therapy: radiobiology meets molecular pathology. Nat Rev Cancer 6: 702-713.
21. Andersen M H, Berglund L, Rasmussen J T, Petersen T E (1997) Bovine PAS-6/7 binds alpha v beta 5 integrins and anionic phospholipids through two domains. Biochemistry 36: 5441-5446.
22. Miksa M, Amin D, Wu R, Ravikumar T S, Wang P (2007) Fractalkine-induced MFG-E8 leads to enhanced apoptotic cell clearance by macrophages. Mol Med 13: 553-560.
23. Shi J, Pipe S W, Rasmussen J T, Heegaard C W, Gilbert G E (2008) Lactadherin blocks thrombosis and hemostasis in vivo: correlation with platelet phosphatidylserine exposure. J Thromb Haemost 6: 1167-1174.
24. Hwang J M, Chan D C, Chang T M, Tsao T Y, Tsou S S, et al. (2003) Effects of oral arginine and glutamine on radiation-induced injury in the rat. J Surg Res 109: 149-154.
25. Chumakov P M (2007) Versatile functions of p53 protein in multicellular organisms. Biochemistry (Mosc) 72: 1399-1421.

26. DeLeo A B, Jay G, Appella E, Dubois G C, Law L W, et al. (1979) Detection of a transformation-related antigen in chemically induced sarcomas and other transformed cells of the mouse. Proc Natl Acad Sci USA 76: 2420-2424.
27. Lane D P, Crawford L V (1979) T antigen is bound to a host protein in SV40-transformed cells. Nature 278: 261-263.
28. Wang B, Xiao Z, Ko H L, Ren E C (2010) The p53 response element and transcriptional repression. Cell Cycle 9: 870-879.
29. Brooks C L, Gu W (2011) p53 regulation by ubiquitin. FEBS Lett 585: 2803-2809.
30. Perry M E (2010) The regulation of the p53-mediated stress response by MDM2 and MDM4. Cold Spring Harb Perspect Biol 2: a000968.
31. Komarova E A, Kondratov R V, Wang K, Christov K, Golovkina T V, et al. (2004) Dual effect of p53 on radiation sensitivity in vivo: p53 promotes hematopoietic injury, but protects from gastro-intestinal syndrome in mice. Oncogene 23: 3265-3271.
32. Rodriguez R, Meuth M (2006) Chk1 and p21 cooperate to prevent apoptosis during DNA replication fork stress. Mol Biol Cell 17: 402-412.
33. Sitko J C, Yeh B, Kim M, Zhou H, Takaesu G, et al. (2008) SOCS3 regulates p21 expression and cell cycle arrest in response to DNA damage. Cell Signal 20: 2221-2230.
34. Huang D C, Adams J M, Cory S (1998) The conserved N-terminal BH4 domain of Bcl-2 homologues is essential for inhibition of apoptosis and interaction with CED-4. Embo J 17: 1029-1039.
35. Kluck R M, Bossy-Wetzel E, Green D R, Newmeyer D D (1997) The release of cytochrome c from mitochondria: a primary site for Bcl-2 regulation of apoptosis. Science 275: 1132-1136.
36. Ruvolo P P, Deng X, May W S (2001) Phosphorylation of Bcl2 and regulation of apoptosis. Leukemia 15: 515-522.
37. Miksa M, Wu R, Dong W, Das P, Yang D, et al. (2006) Dendritic cell-derived exosomes containing milk fat globule epidermal growth factor-factor VIII attenuate proinflammatory responses in sepsis. Shock 25: 586-593.
38. Miksa M, Wu R, Dong W, Komura H, Amin D, et al. (2009) Immature dendritic cell-derived exosomes rescue septic animals via milk fat globule epidermal growth factor VIII. J Immunol 183: 5983-5990.
39. Hanayama R, Tanaka M, Miwa K, Shinohara A, Iwamatsu A, et al. (2002) Identification of a factor that links apoptotic cells to phagocytes. Nature 417: 182-187.
40. Aziz M, Jacob A, Matsuda A, Wu R, Zhou M, et al. (2011) Pre-treatment of recombinant mouse MFG-E8 downregulates LPS-induced TNF-alpha production in macrophages via STAT3-mediated SOCS3 activation. PLoS One 6: e27685.
41. Li Q, Martinez J D (2011) Loss of HSF1 results in defective radiation-induced G(2) arrest and DNA repair. Radiat Res 176: 17-24.

What is claimed is:

1. A method of treating radiation damage in a subject exposed to radiation therapy for treatment of a disease comprising administering to the subject a milk fat globule epidermal growth factor-factor VIII (MFG-E8) in an amount effective to reduce radiation-induced intestinal epithelial cell death in a subject following exposure to radiation therapy for treatment of a disease, wherein MFG-E8 is administered to the subject either before radiation therapy or within 24 hours after onset of radiation therapy.

2. The method of claim 1, wherein the disease is cancer.

3. The method of claim 1, wherein treatment of the subject with MFG-E8 reduces a decrease in body weight following exposure to radiation.

4. The method of claim 1, wherein treatment of the subject with MFG-E8 reduces a decrease in MFG-E8 following exposure to radiation.

5. The method of claim 1, wherein the MFG-E8 is a recombinant human MFG-E8 (rhMFG-E8).

6. The method of claim 5, wherein the rhMFG-E8 has an amino acid sequence that is at least 95% identical to human MFG-E8 (hMFG-E8) (SEQ ID NO:1).

7. The method of claim 1, wherein the MFG-E8 is a human MFG-E8.

8. The method of claim 7, wherein the MFG-E8 has an amino acid sequence that is at least 95% identical to human MFG-E8 (SEQ ID NO:1).

9. The method of claim 1, wherein the MFG-E8 is non-glycosylated.

10. The method of claim 1, wherein the subject does not have sepsis.

* * * * *

SEQUENCE LISTING

```
<160> NUMBER OF SEQ ID NOS: 12

<210> SEQ ID NO 1
<211> LENGTH: 364
<212> TYPE: PRT
<213> ORGANISM: Homo sapiens

<400> SEQUENCE: 1

Leu Asp Ile Cys Ser Lys Asn Pro Cys His Asn Gly Gly Leu Cys Glu
1               5                   10                  15

Glu Ile Ser Gln Glu Val Arg Gly Asp Val Phe Pro Ser Tyr Thr Cys
            20                  25                  30

Thr Cys Leu Lys Gly Tyr Ala Gly Asn His Cys Glu Thr Lys Cys Val
        35                  40                  45

Glu Pro Leu Gly Met Glu Asn Gly Asn Ile Ala Asn Ser Gln Ile Ala
    50                  55                  60

Ala Ser Ser Val Arg Val Thr Phe Leu Gly Leu Gln His Trp Val Pro
65                  70                  75                  80

Glu Leu Ala Arg Leu Asn Arg Ala Gly Met Val Asn Ala Trp Thr Pro
                85                  90                  95

Ser Ser Asn Asp Asp Asn Pro Trp Ile Gln Val Asn Leu Leu Arg Arg
            100                 105                 110

Met Trp Val Thr Gly Val Val Thr Gln Gly Ala Ser Arg Leu Ala Ser
        115                 120                 125

His Glu Tyr Leu Lys Ala Phe Lys Val Ala Tyr Ser Leu Asn Gly His
    130                 135                 140

Glu Phe Asp Phe Ile His Asp Val Asn Lys Lys His Lys Glu Phe Val
145                 150                 155                 160

Gly Asn Trp Asn Lys Asn Ala Val His Val Asn Leu Phe Glu Thr Pro
                165                 170                 175
```

```
Val Glu Ala Gln Tyr Val Arg Leu Tyr Pro Thr Ser Cys His Thr Ala
            180                 185                 190

Cys Thr Leu Arg Phe Glu Leu Leu Gly Cys Glu Leu Asn Gly Cys Ala
            195                 200                 205

Asn Pro Leu Gly Leu Lys Asn Asn Ser Ile Pro Asp Lys Gln Ile Thr
210                 215                 220

Ala Ser Ser Ser Tyr Lys Thr Trp Gly Leu His Leu Phe Ser Trp Asn
225                 230                 235                 240

Pro Ser Tyr Ala Arg Leu Asp Lys Gln Gly Asn Phe Asn Ala Trp Val
            245                 250                 255

Ala Gly Ser Tyr Gly Asn Asp Gln Trp Leu Gln Val Asp Leu Gly Ser
            260                 265                 270

Ser Lys Glu Val Thr Gly Ile Ile Thr Gln Gly Ala Arg Asn Phe Gly
            275                 280                 285

Ser Val Gln Phe Val Ala Ser Tyr Lys Val Ala Tyr Ser Asn Asp Ser
            290                 295                 300

Ala Asn Trp Thr Glu Tyr Gln Asp Pro Arg Thr Gly Ser Ser Lys Ile
305                 310                 315                 320

Phe Pro Gly Asn Trp Asp Asn His Ser His Lys Lys Asn Leu Phe Glu
            325                 330                 335

Thr Pro Ile Leu Ala Arg Tyr Val Arg Ile Leu Pro Val Ala Trp His
            340                 345                 350

Asn Arg Ile Ala Leu Arg Leu Glu Leu Leu Gly Cys
            355                 360

<210> SEQ ID NO 2
<211> LENGTH: 387
<212> TYPE: PRT
<213> ORGANISM: Homo sapiens

<400> SEQUENCE: 2

Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Asp
            35                  40                  45

Val Phe Pro Ser Tyr Thr Cys Thr Cys Leu Lys Gly Tyr Ala Gly Asn
            50                  55                  60

His Cys Glu Thr Lys Cys Val Glu Pro Leu Gly Met Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
            115                 120                 125

Gln Val Asn Leu Leu Arg Arg Met Trp Val Thr Gly Val Val Thr Gln
130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
```

```
                    180                 185                 190
Val Asn Leu Phe Glu Thr Pro Val Glu Ala Gln Tyr Val Arg Leu Tyr
                195                 200                 205

Pro Thr Ser Cys His Thr Ala Cys Thr Leu Arg Phe Glu Leu Leu Gly
            210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Tyr Lys Thr Trp Gly
                245                 250                 255

Leu His Leu Phe Ser Trp Asn Pro Ser Tyr Ala Arg Leu Asp Lys Gln
                260                 265                 270

Gly Asn Phe Asn Ala Trp Val Ala Gly Ser Tyr Gly Asn Asp Gln Trp
            275                 280                 285

Leu Gln Val Asp Leu Gly Ser Ser Lys Glu Val Thr Gly Ile Ile Thr
        290                 295                 300

Gln Gly Ala Arg Asn Phe Gly Ser Val Gln Phe Val Ala Ser Tyr Lys
305                 310                 315                 320

Val Ala Tyr Ser Asn Asp Ser Ala Asn Trp Thr Glu Tyr Gln Asp Pro
                325                 330                 335

Arg Thr Gly Ser Ser Lys Ile Phe Pro Gly Asn Trp Asp Asn His Ser
            340                 345                 350

His Lys Lys Asn Leu Phe Glu Thr Pro Ile Leu Ala Arg Tyr Val Arg
        355                 360                 365

Ile Leu Pro Val Ala Trp His Asn Arg Ile Ala Leu Arg Leu Glu Leu
370                 375                 380

Leu Gly Cys
385

<210> SEQ ID NO 3
<211> LENGTH: 463
<212> TYPE: PRT
<213> ORGANISM: Mus musculus

<400> SEQUENCE: 3

Met Gln Val Ser Arg Val Leu Ala Ala Leu Cys Gly Met Leu Leu Cys
1               5                   10                  15

Ala Ser Gly Leu Phe Ala Ala Ser Gly Asp Phe Cys Asp Ser Ser Leu
                20                  25                  30

Cys Leu Asn Gly Gly Thr Cys Leu Thr Gly Gln Asp Asn Asp Ile Tyr
            35                  40                  45

Cys Leu Cys Pro Glu Gly Phe Thr Gly Leu Val Cys Asn Glu Thr Glu
        50                  55                  60

Arg Gly Pro Cys Ser Pro Asn Pro Cys Tyr Asn Asp Ala Lys Cys Leu
65                  70                  75                  80

Val Thr Leu Asp Thr Gln Arg Gly Asp Ile Phe Thr Glu Tyr Ile Cys
                85                  90                  95

Gln Cys Pro Val Gly Tyr Ser Gly Ile His Cys Glu Thr Glu Thr Asn
                100                 105                 110

Tyr Tyr Asn Leu Asp Gly Glu Tyr Met Phe Thr Thr Ala Val Pro Asn
            115                 120                 125

Thr Ala Val Pro Thr Pro Ala Pro Thr Pro Asp Leu Ser Asn Asn Leu
        130                 135                 140

Ala Ser Arg Cys Ser Thr Gln Leu Gly Met Glu Gly Gly Ala Ile Ala
145                 150                 155                 160
```

```
Asp Ser Gln Ile Ser Ala Ser Tyr Val Tyr Met Gly Phe Met Gly Leu
            165                 170                 175
Gln Arg Trp Gly Pro Glu Leu Ala Arg Leu Tyr Arg Thr Gly Ile Val
        180                 185                 190
Asn Ala Trp His Ala Ser Asn Tyr Asp Ser Lys Pro Trp Ile Gln Val
    195                 200                 205
Asn Leu Leu Arg Lys Met Arg Val Ser Gly Val Met Thr Gln Gly Ala
210                 215                 220
Ser Arg Ala Gly Arg Ala Glu Tyr Leu Lys Thr Phe Lys Val Ala Tyr
225                 230                 235                 240
Ser Leu Asp Gly Arg Lys Phe Glu Phe Ile Gln Asp Glu Ser Gly Gly
            245                 250                 255
Asp Lys Glu Phe Leu Gly Asn Leu Asp Asn Asn Ser Leu Lys Val Asn
        260                 265                 270
Met Phe Asn Pro Thr Leu Glu Ala Gln Tyr Ile Arg Leu Tyr Pro Val
    275                 280                 285
Ser Cys His Arg Gly Cys Thr Leu Arg Phe Glu Leu Leu Gly Cys Glu
290                 295                 300
Leu His Gly Cys Leu Glu Pro Leu Gly Leu Lys Asn Asn Thr Ile Pro
305                 310                 315                 320
Asp Ser Gln Met Ser Ala Ser Ser Tyr Lys Thr Trp Asn Leu Arg
            325                 330                 335
Ala Phe Gly Trp Tyr Pro His Leu Gly Arg Leu Asp Asn Gln Gly Lys
            340                 345                 350
Ile Asn Ala Trp Thr Ala Gln Ser Asn Ser Ala Lys Glu Trp Leu Gln
        355                 360                 365
Val Asp Leu Gly Thr Gln Arg Gln Val Thr Gly Ile Ile Thr Gln Gly
370                 375                 380
Ala Arg Asp Phe Gly His Ile Gln Tyr Val Glu Ser Tyr Lys Val Ala
385                 390                 395                 400
His Ser Asp Asp Gly Val Gln Trp Thr Val Tyr Glu Glu Gln Gly Ser
            405                 410                 415
Ser Lys Val Phe Gln Gly Asn Leu Asp Asn Asn Ser His Lys Lys Asn
        420                 425                 430
Ile Phe Glu Lys Pro Phe Met Ala Arg Tyr Val Arg Val Leu Pro Val
    435                 440                 445
Ser Trp His Asn Arg Ile Thr Leu Arg Leu Glu Leu Leu Gly Cys
450                 455                 460

<210> SEQ ID NO 4
<211> LENGTH: 1095
<212> TYPE: DNA
<213> ORGANISM: Homo sapiens

<400> SEQUENCE: 4
ctggatatct gttccaaaaa cccctgccac aacggtggtt tatgcgagga gatttcccaa      60
gaagtgcgag gagatgtctt cccctcgtac acctgcacgt gccttaaggg ctacgcgggc     120
aaccactgtg agacgaaatg tgtcgagcca ctgggcatgg agaatgggaa cattgccaac     180
tcacagatcg ccgcctcatc tgtgcgtgtg accttcttgg gtttgcagca ttgggtcccg     240
gagctggccc gcctgaaccg cgcaggcatg gtcaatgcct ggacacccag cagcaatgac     300 gataaccccct ggatccaggt gaacctgctg cggaggatgt gggtaacagg tgtggtgacg     360
cagggtgcca gccgcttggc cagtcatgag tacctgaagg ccttcaaggt ggcctacagc     420
```

-continued

```
cttaatggac acgaattcga tttcatccat gatgttaata aaaaacacaa ggagtttgtg      480
ggtaactgga acaaaaacgc ggtgcatgtc aacctgtttg agaccccagt ggaggctcag      540
tacgtgagat tgtaccccac gagctgccac acggcctgca ctctgcgctt tgagctactg      600
ggctgtgagc tgaacggatg cgccaatccc ctgggcctga agaataacag catccctgac      660
aagcagatca cggcctccag cagctacaag acctggggct tgcatctctt cagctggaac      720
ccctcctatg cacggctgga caagcagggc aacttcaacg cctgggttgc ggggagctac      780
ggtaacgatc agtggctgca ggtggacctg ggctcctcga aggaggtgac aggcatcatc      840 acccagggggg cccgtaactt tggctctgtc cagtttgtgg catcctacaa ggttgcctac      900
agtaatgaca gtgcgaactg gactgagtac caggacccca ggactggcag cagtaagatc      960
ttccctggca actgggacaa ccactccac aagaagaact tgtttgagac gcccatcctg     1020
gctcgctatg tgcgcatcct gcctgtagcc tggcacaacc gcatcgccct gcgcctggag     1080
ctgctgggct gttag                                                      1095
```

```
<210> SEQ ID NO 5
<211> LENGTH: 18
<212> TYPE: DNA
<213> ORGANISM: Artificial
<220> FEATURE:
<223> OTHER INFORMATION: forward primer for MFG-E8

<400> SEQUENCE: 5
tgaggaacaa ggaaccag                                                     18

<210> SEQ ID NO 6
<211> LENGTH: 18
<212> TYPE: DNA
<213> ORGANISM: Artificial
<220> FEATURE:
<223> OTHER INFORMATION: reverse primer for MFG-E8

<400> SEQUENCE: 6
ggaaggacac gcacatag                                                     18

<210> SEQ ID NO 7
<211> LENGTH: 19
<212> TYPE: DNA
<213> ORGANISM: Artificial
<220> FEATURE:
<223> OTHER INFORMATION: forward primer for p53

<400> SEQUENCE: 7
ccccaccgcc tgtaagatt                                                    19

<210> SEQ ID NO 8
<211> LENGTH: 21
<212> TYPE: DNA
<213> ORGANISM: Artificial
<220> FEATURE:
<223> OTHER INFORMATION: reverse primer for p53

<400> SEQUENCE: 8
atgggtccgg aggatacaga t                                                 21

<210> SEQ ID NO 9
<211> LENGTH: 17
<212> TYPE: DNA
<213> ORGANISM: Artificial
<220> FEATURE:
<223> OTHER INFORMATION: forward primer for p21
```

```
<400> SEQUENCE: 9
cgggaccggg acatctc                                                      17

<210> SEQ ID NO 10
<211> LENGTH: 20
<212> TYPE: DNA
<213> ORGANISM: Artificial
<220> FEATURE:
<223> OTHER INFORMATION: reverse primer for p21

<400> SEQUENCE: 10
cggcgcttgg agtgatagaa                                                   20

<210> SEQ ID NO 11
<211> LENGTH: 26
<212> TYPE: DNA
<213> ORGANISM: Artificial
<220> FEATURE:
<223> OTHER INFORMATION: forward primer for G3PDH

<400> SEQUENCE: 11
tgaaggtcgg tgtcaacgga tttggc                                            26

<210> SEQ ID NO 12
<211> LENGTH: 24
<212> TYPE: DNA
<213> ORGANISM: Artificial
<220> FEATURE:
<223> OTHER INFORMATION: reverse primer for G3PDH

<400> SEQUENCE: 12
catgtaggcc atgaggtcca ccac                                              24
```